(12) United States Patent
Qian et al.

(10) Patent No.: US 6,869,803 B2
(45) Date of Patent: Mar. 22, 2005

(54) METHOD TO QUANTITATIVELY ANALYZE CONJUGATED DIENES IN HYDROCARBON FEEDS AND PRODUCTS AS AN INDICATOR OF FOULING POTENTIAL

(75) Inventors: Kuangnan Qian, Belle Mead, NJ (US); Kathleen E. Edwards, Freehold, NJ (US); Frank C. Wang, Annandale, NJ (US); Michael Siskin, Randolph, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/458,456

(22) Filed: Jun. 10, 2003

(65) Prior Publication Data

US 2004/0029287 A1 Feb. 12, 2004

Related U.S. Application Data

(60) Provisional application No. 60/401,377, filed on Aug. 6, 2002.

(51) Int. Cl.[7] ............................................. G01N 33/00

(52) U.S. Cl. ...................... 436/142; 436/29; 436/139; 436/161; 436/173; 436/174

(58) Field of Search ......................... 436/142, 29, 139, 436/161, 172–174

(56) References Cited

PUBLICATIONS

Christie, W.W. "Mass spectra of methyl esters of fatty acids—further derivatization" http://www.lipid.co.uk/infores/ms/ms04/, Oct. 4, 2001.*

Christie, "Mass Spectra of Methyl Esters of Fatty Acids—Further Derivatization", http://www.lipid.co.uk/infores/ms/ms04/file.pdf, May 9, 2000, pp. 1–7, especially pp. 2–5.

* cited by examiner

Primary Examiner—Yelena G. Gakh
(74) Attorney, Agent, or Firm—Ronald D. Hantman

(57) ABSTRACT

A method to quantify the conjugated dienes in a feedstream including the steps of dissolving 4-methyl-1,2,4-trazoline-3,5-dione (MTAD) in said feedstream, and determining the molar concentration of said conjugated dienes and/or the carbon number distribution of said conjugated dienes by GC/MS and GC/NCD (Nitrogen Chemiluminescence Detection).

8 Claims, 5 Drawing Sheets

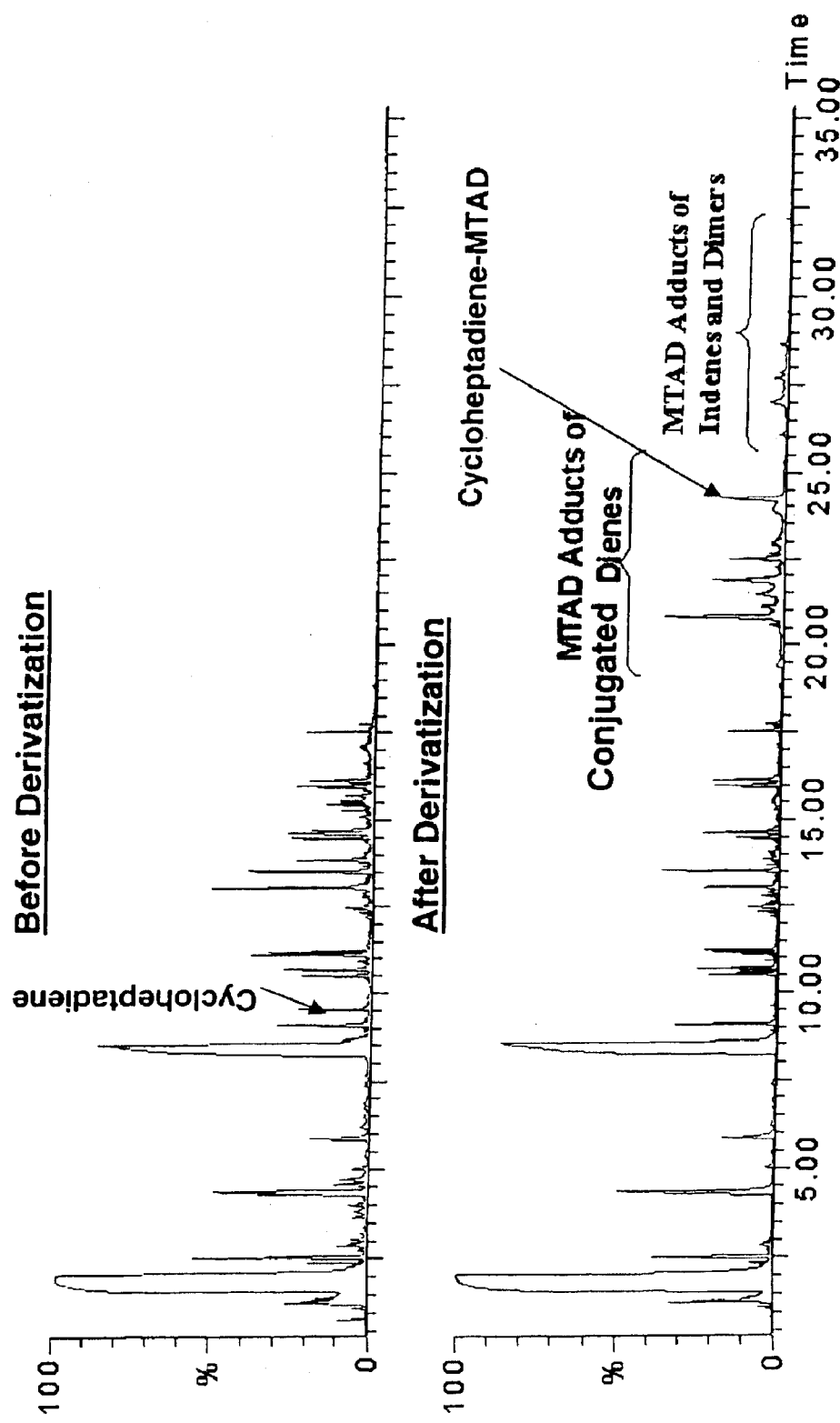
Figure 1. GC/MS Chromatogram of Steam Cracked Naphtha Plus Cycloheptadiene Internal Standard Before and After MTAD Derivatization

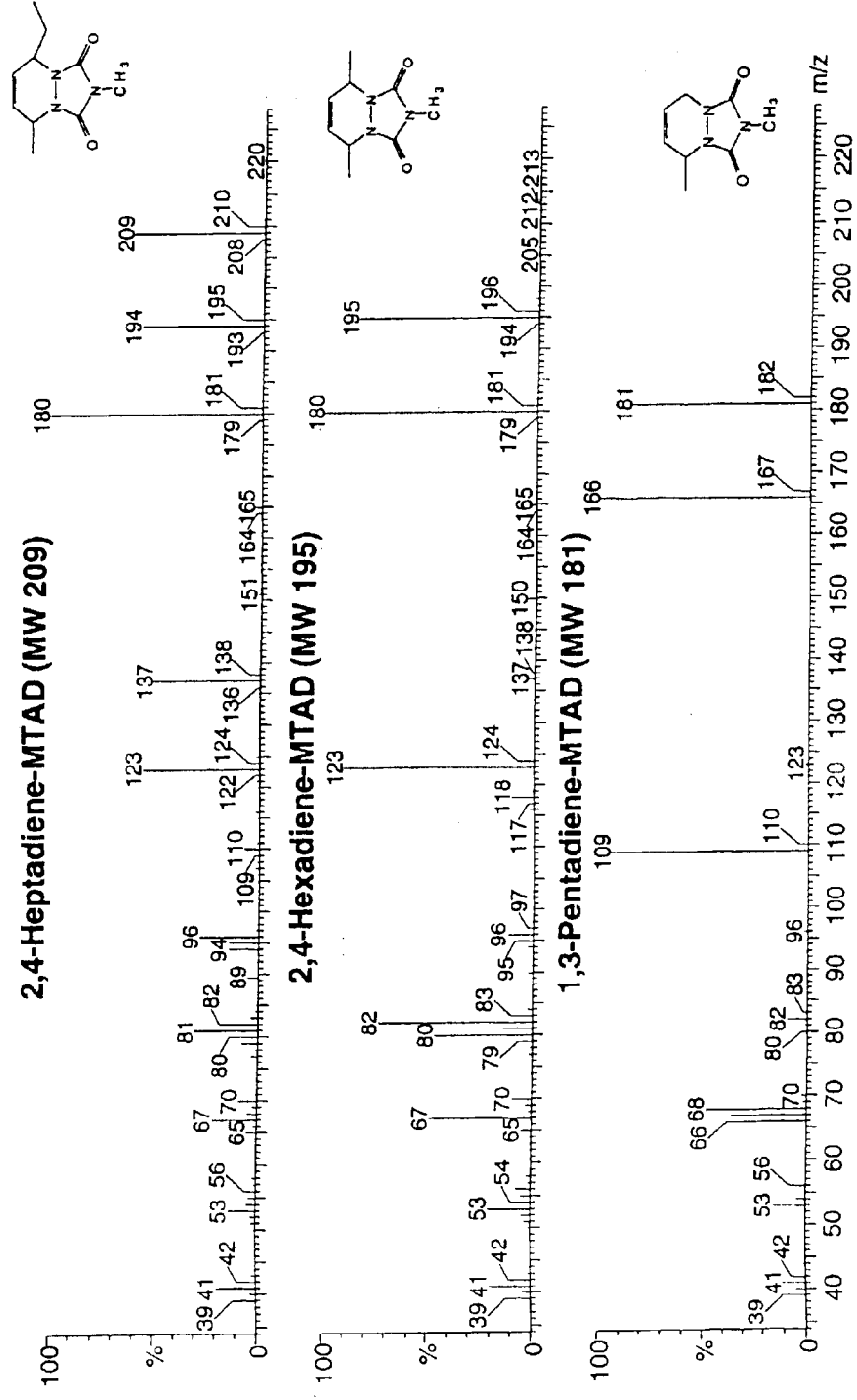
Figure 2. GC/MS Spectra (Electron Impact) of MTAD Adducts of 2,4-Heptadiene, 2,4-Hexadiene and 1,3-Pentadiene

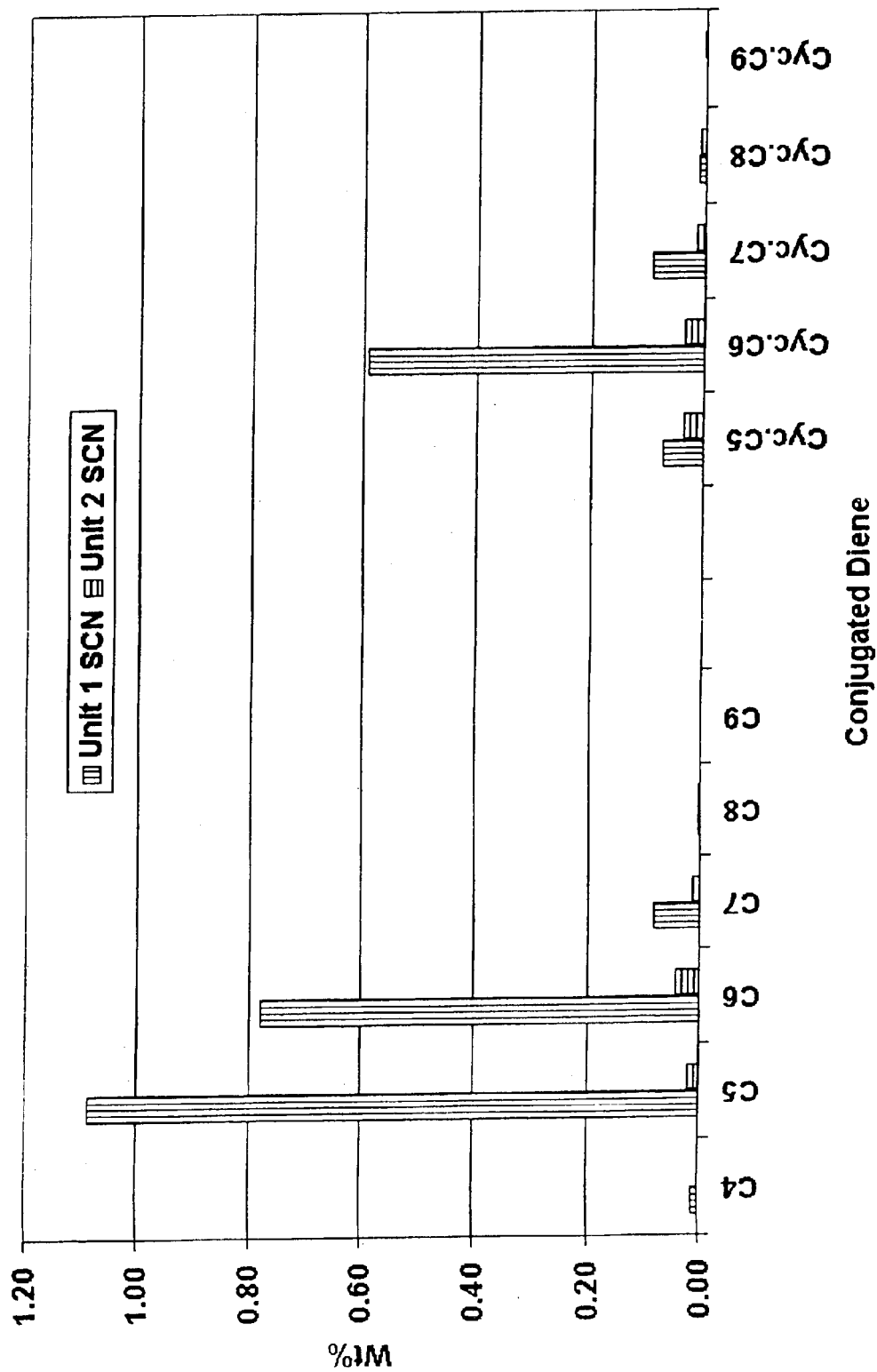
Figure 3. Conjugated Dienes in SCN Before and After Hydrotreating (H/T) as Determined by MTAD-GC/MS Method

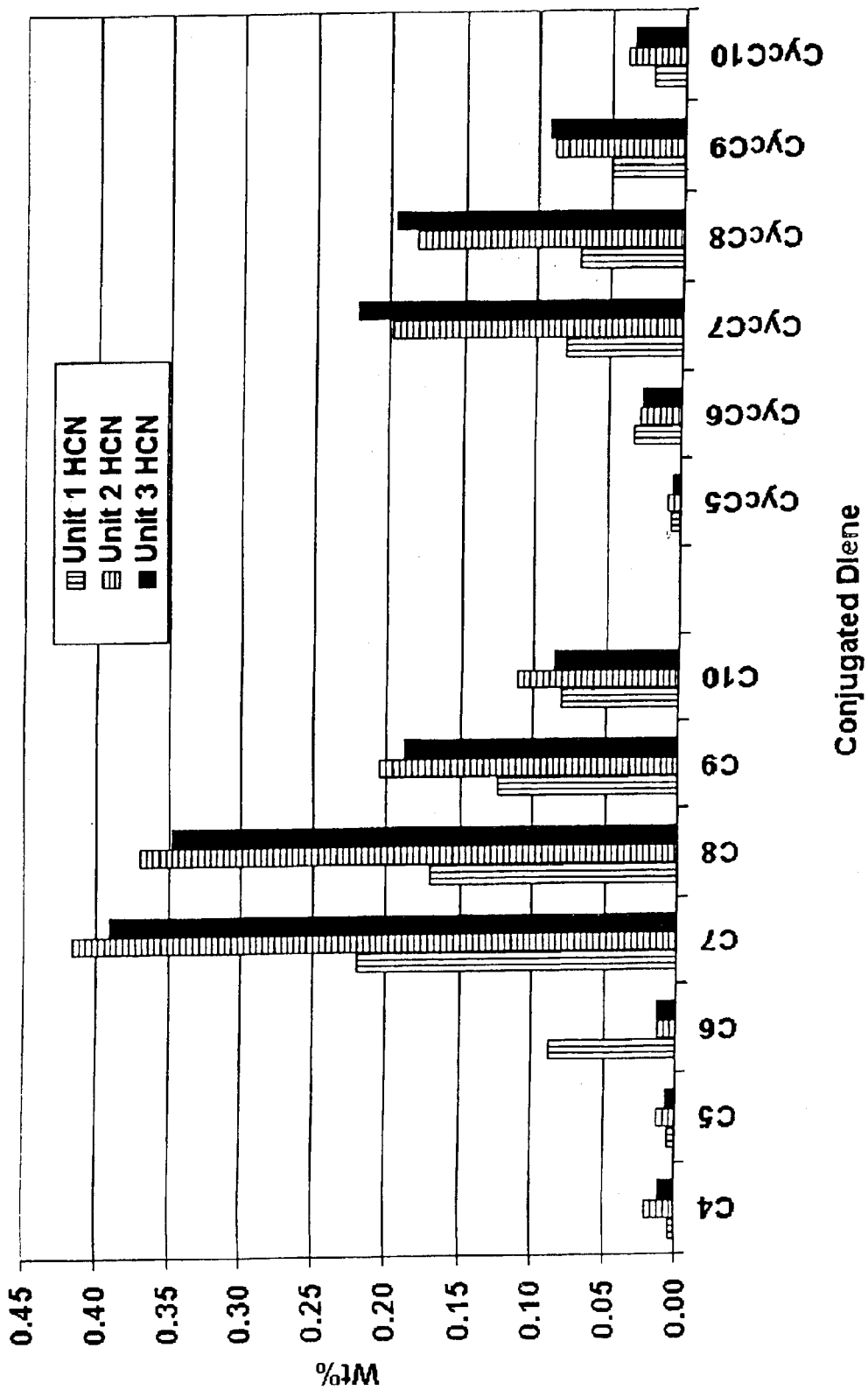
Figure 4. Conjugated Dienes in HCN as Determined by MTAD-GC/MS Method

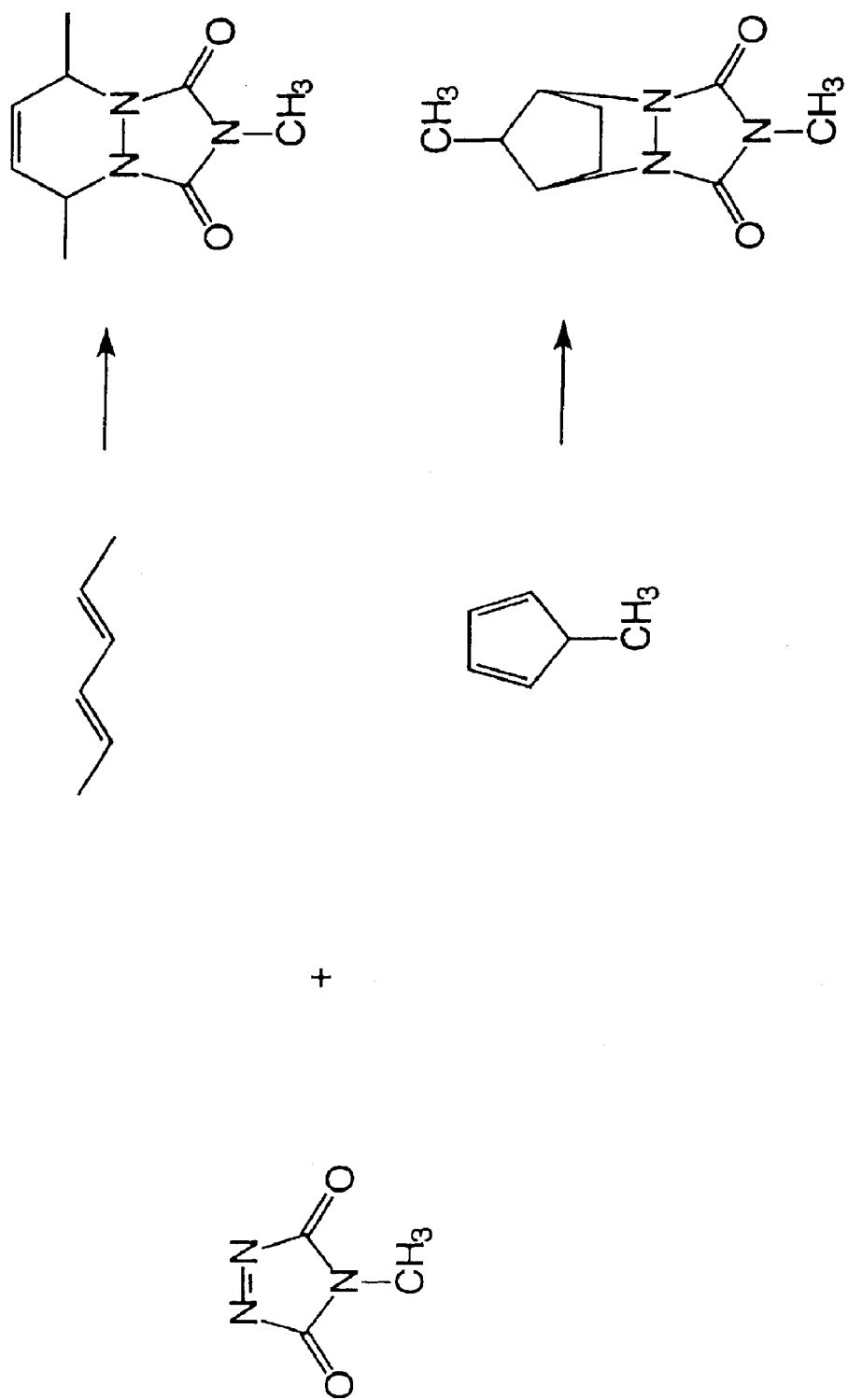
Figure 5. MTAD conjugated diene reaction scheme

METHOD TO QUANTITATIVELY ANALYZE CONJUGATED DIENES IN HYDROCARBON FEEDS AND PRODUCTS AS AN INDICATOR OF FOULING POTENTIAL

This application is a Non-Provisional of Provisional U.S. Ser. No. 60/401,377 filed Aug. 6, 2002.

BACKGROUND OF THE INVENTION

The present invention is related to a method to quantify conjugated dienes in hydrocarbon feedstream and product. In particular, the method determines the molar concentration and/or the carbon number distribution of the conjugated dienes.

Conjugated dienes are a major class of compounds in hydrocarbon systems that are responsible for deposit formation in refinery conversion units such as hydrocracking and hydroconversion conversion units and fractionators and heat exchangers. They are also responsible for deposit formation in automobile engines. The information is critical for assessing the potential of forming deposits in a hydrocarbon system. Knowledge of the concentration and types of conjugated dienes provides guidance to the refinery on the necessity of pretreating the refinery feed, such as installing a diolefin saturator prior to processing in order to prevent fouling during processing. In fuel applications, the information may be used to determine, e.g. if and how much a naphtha can be blended into fuel or if the naphtha needs to be hydrotreated, etc.

There are no reliable established methods to identify and quantify conjugated dienes, acyclic and cyclic, in hydrocarbon systems. GC/FID can be used to quantify small conjugated dienes (Less than $C_6$) in low boiling hydrocarbon systems. The identifications were made based on retention times and mass spectral library matches. The method cannot identify/quantify large conjugated dienes (Greater than $C_6$) due to the low concentrations of the analytes, severe overlaps with other hydrocarbon components and very similar mass spectra between conjugated and non-conjugated dienes.

Bromination has been widely used to determine olefin content (including conjugated dienes) in hydrocarbons. It can not differentiate conjugated dienes from other olefins. Aromatics, especially phenols, can interfere with the analysis.

The MAV test is a semiquantitative method developed by UOP and uses maleic anhydride as a derivatization agent. The reaction is not selective and cannot proceed quantitatively. Therefore, only a relative number can be obtained. In addition, it cannot provide molecular identifications of different conjugated diene types required for refinery guidance.

SUMMARY OF THE INVENTION

The present invention is a method that detects, identifies and quantifies conjugated dienes in various hydrocarbon matrices, such as steam cracked naphtha, catalytic cracked naphtha, coker naphthas, and other petroleum distillates. Conjugated dienes are largely responsible for molecular weight growth reactions (fouling) in various refinery processes.

The invention described herein is based on selective and rapid room temperature derivatization of conjugated dienes by 4-methyl-1,2,4-triazoline-3,5-dione (MTAD) followed by Chemical ionization GC/MS and GC/NCD analyses. The method is highly selective and sensitive to linear, branched and cyclic conjugated dienes with no interference from other hydrocarbon components. The invention has been successfully applied to the determination of the types and concentrations of conjugated dienes in steam cracked and catalytic cracked naphthas.

BRIEF DESCRIPTION OF THE DRAWINGS

FIG. 1 shows a GC/MS chromatogram of steam cracked naphtha (SCN) plus cycloheptadiene internal standard before and after MTAD derivatization.

FIG. 2 shows a GC/MS spectra (electron impact) of MTAD adducts of 2,4-heptadiene, 2,4-hexadiene and 1,3-pentadiene.

FIG. 3 shows the conjugated diene distributions in two steam cracked naphthas (SCN).

FIG. 4 shows the conjugated diene distributions in three heavy catalytic naphthas (HCN).

FIG. 5 shows a schematic of the reaction of MTAD with a linear and cyclic conjugated diene.

DETAILED DESCRIPTION OF THE PREFERRED EMBODIMENTS

The present invention is a method that can detect, identify and quantify trace levels of conjugated dienes in fuel, petroleum feeds and products. These conjugated structures are largely responsible for the molecular weight growth reactions (fouling) in refinery units and deposit formation in automobile engines. Complete identification/quantification of the conjugated dienes types are needed for fouling prevention and management. The method includes the following: (1) Selective and quantitative chemical derivatization of conjugated dienes by 4-methyl-1,2,4-triazoline-3,5-dione (MTAD); (2) selective and quantitative determination of MTAD-diene adducts as a function of carbon number by Chemical Ionization (Gas Chromatagraph/Mass Spectrometry (CI GC/MS); and (3) the determination of total conjugated dienes by GC with a nitrogen selective detector, such as Gas Chromatagraph/Nitrogen Chemiluminescence Detector (GC/NCD).

General Procedure

MTAD stock solution was prepared by dissolving 250 mg of MTAD in 5 ml of methylene chloride. The stock solution was directly mixed with hydrocarbon samples at room temperature to derivatize the conjugated structures. MTAD selectively and rapidly (usually <5 seconds) reacts with linear and cyclic conjugated dienes as illustrated in FIG. 5.

Cycloheptadiene was chosen as an internal standard for quantification purposes. The derivatized samples were analyzed by GC/NCD to determine the total molar concentration of conjugated dienes. The derivatized samples were also analyzed in parallel by GC/MS to determine carbon number distribution of conjugated dienes. Molecules were ionized by Chemical ionization (CI) using deuterated amonia ($ND_3$). Selected ion display of deuterated molecular ion $[M+D^+]$ and $ND_4$ adduct $[M+ND_4^+]$ was used to differentiate various conjugated dienes.

MTAD forms a 1:1 adduct with linear and cyclic conjugated dienes. FIG. 1 shows a GC/MS chromatogram of steam cracked naphtha before and after the derivatization. A series of peaks showing up at retention times after 20 minutes are due to the formation of MTAD reaction products. The chromatography peaks before 20 minutes were significantly simplified; also an indication of derivatization. Styrenes, indenes and dimers of CPD and MCPD partially react with MTAD. They form MTAD-adducts at retention times greater than 26 minutes. Non-conjugated hydrocarbons do not react with MTAD under said experimental conditions.

It was noted that the retention time of the diene adducts is mainly influenced by the polarity of the compounds rather than by their molecular weight. This has complicated the analysis because conjugated dienes with different carbon numbers can overlap in chromatography. GC/MS becomes necessary to differentiate the conjugated dienes.

MTAD: Dienes Ratio

The effect of MTAD loading on the MTAD derivatization was evaluated by both GC/NCD and GC/MS. For the model compound 1,3 hexadiene, 100% conversion is reached when the molar concentration of MTAD to the conjugated diene is between 2 to 10. When the ratio is below 2, MTAD reaction is incomplete. When the ratio is greater than 10, self-polymerization of MTAD becomes predominant and results in the reduction of MTAD-conjugated diene adducts.

The excess MTAD loading becomes a greater problem for real sample analyses. It causes formation of MTAD derivatives that are not due to conjugated dienes. It is concluded that the optimum MTAD: conjugated diene ratio is between 2 and 3.5 for quantitative analyses.

Relative Sensitivities

We initially evaluated the relative sensitivity of 12 model compounds of conjugated dienes by GC/NCD, GC/FID and EI-GC/MS. GC/NCD gives quite uniform responses. The molecular ion intensities of EI-GC/MS, however, vary significantly. Since CI is a soft ionization method, which does not fragment molecules as much as EI, we evaluated CI-GC/MS using $CH_4$ and $ND_3$ as reagent gases for five-selected model compounds. Variation in response factor is indeed reduced and becomes more predictable. Both reagent gases yield similar relative response factors. In $CH_4$ CI, molecules tend to form protonated molecular ions $[M+H^+]$ and ethyl cation adducts $[M+C_2H_9^+]$, which can cause mass overlaps for dienes with different carbon numbers, e.g. $C_5+C_2H_9^+$ overlap with $C_7+H^+$. $ND_3$ CI does not have the problem and was chosen for the analyses.

Determination of Conjugated Diene Structures

The method provides structural information on conjugated dienes that cannot be obtained by any existing techniques. The mass spectra of the conjugated diene adducts are characteristic of the double bond positions and their chemical environment. FIG. 2 illustrates the mass spectra of MTAD adducts of 1,3-pentadiene, 2,4-hexadiene and 2,4-hepdiene.

Analysis of Naphtha Samples

The MTAD method can detect up to $C_{10}$ conjugated dienes. We have applied the method to various naphtha samples. FIG. 3 shows the conjugated diene distributions in two Steam Cracked Naphthas (SCN); raw and hydrotreated samples. Most conjugated dienes, both acyclic and cyclic, are $C_5$–$C_7$ in these SCN samples, which are invisible to GC/FID.

FIG. 4 shows a similar set of distributions for conjugated dienes in three heavy catalytic naphthas (HCN). Most conjugated dienes both acyclic and cyclic, are $C_7^+$ in these samples.

What is claimed is:

1. A method to quantify the conjugated dienes in a feed or product stream comprising:
    (a) dissolving 4-methyl-1,2,4-trazoline-3,5-dione (MTAD) in said feedstream,
    (b) using a reference compound to determine the molar concentration of said conjugated dienes in said feed or product stream and the carbon number distribution of said conjugated dienes by Chemical Ionization Gas Chromatography/Mass Spectrometry (CI GC/MS), and
    (c) determining total conjugated dienes by GC with a nitrogen selective detector.

2. The method of claim 1, wherein step (c) comprises determining total conjugated dienes by GC with Nitrogen Chemiluminescence Detection (GC/NCD).

3. The process of claim 1 wherein the MTAD: conjugated diene ratio is between 2 to 10.

4. The process of claim 1 wherein the MTAD: conjugated diene ratio is between 2 and 3.5.

5. The process of claim 1 wherein an on-line gas chromatograph (GC) is used to separate isomeric components of MTAD-conjugated diene adducts by polarity.

6. The process of claim 1 wherein all MTAD-conjugated diene molecules, cyclic and acyclic form $[M+D^+]$ and $[M+ND_4^+]$ ions in $ND_3$ Chemical ionization.

7. The process of claim 1, wherein the carbon number distribution is determined for dienes comprising up to ten carbon atoms.

8. A method to quantify the conjugated dienes and their carbon number distribution in feed or product stream comprising:
    (a) Introducing a reference compound to feed or product stream as quantification standard;
    (b) Dissolving 4-methyl-1,2,4-trazoline-3,5-dione (MTAD) in feed or product stream to chemically derivatize the conjugated diene components;
    (c) Introducing the MTAD derivatized sample into a gas chromatograph or other means to separate molecules by chemical structure;
    (d) Determining total conjugated dienes by Gas Chromatograph/Nitrogen Chemiluminescence Detector (GC-NCD); and
    (e) Determining the molar concentration of said conjugated dienes and/or the carbon number distributions of the said conjugated dienes by $ND_3$ chemical ionization Gas Chromatograph/Mass Spectrometry (GC/MS).

* * * * *